United States Patent [19]

So et al.

[11] Patent Number: 5,489,521
[45] Date of Patent: Feb. 6, 1996

[54] MUTANT HAVING ICE NUCLEATING ACTIVITY AT ROOM TEMPERATURE AND METHOD FOR MAKING SNOW AND ICE USING IT

[75] Inventors: Sung So, Paldal-ku; Sung Y. Ha, Bisan 3-dong; Moo S. Kim, Kyunggi-do, all of Rep. of Korea

[73] Assignee: Pacific Corporation, Seoul, Rep. of Korea

[21] Appl. No.: 281,033

[22] Filed: Jul. 27, 1994

[30] Foreign Application Priority Data

Jul. 27, 1993 [KR] Rep. of Korea .................. 1993-14322

[51] Int. Cl.$^6$ ..................................... C12N 1/20
[52] U.S. Cl. ................... 435/252.34; 435/168; 435/874; 424/93.47
[58] Field of Search .................. 424/93 N; 435/252.34, 435/168, 874

[56] References Cited

U.S. PATENT DOCUMENTS

| | | | |
|---|---|---|---|
| 4,200,228 | 4/1980 | Woerpel | 239/25 |
| 4,706,463 | 11/1987 | Lindsey | 62/64 |
| 4,796,805 | 1/1989 | Carlberg et al. | 239/2.2 |
| 4,978,540 | 12/1990 | Lee | 426/61 |

OTHER PUBLICATIONS

Principles of Fermentation Technology, Starbury, P & Whitaker, A, Pergamon Press, New York 1984.

*Primary Examiner*—Marian C. Knode
*Assistant Examiner*—Jean C. Witz
*Attorney, Agent, or Firm*—Foley & Lardner

[57] ABSTRACT

Disclosed herein are a new mutant of Pseudomonads having ice nucleating activity and an improved method for making snow and ice using it. More particularly, *Pseudomonas syringae* SO754 of the present invention, which is derived from the parent strain, *Pseudomonas syringae* SO7 can retain its ice nucleating activity at room temperature.

Further, *Pseudomonas syringae* SO754 of the invention retains its high activity during the fermentation, recovery and drying steps and during the storage without freezing treatment.

14 Claims, No Drawings

MUTANT HAVING ICE NUCLEATING ACTIVITY AT ROOM TEMPERATURE AND METHOD FOR MAKING SNOW AND ICE USING IT

BACKGROUND OF THE INVENTION

1. Field of the invention

The present invention relates to a new mutant having ice nucleating activity and an improved method for making snow and ice using it. More particularly, the present invention relates to a new mutant, *Pseudomonas syringae* whose ice nucleating activity is stable at room temperature and relates to an improved method for making snow and ice using it.

2. Description of the Prior Art

In U.S. Pat. No. 4,200,228, there is disclosed a method for the making of snow by suspending and then spraying microorganisms into the air. The microorganisms that are employed in this invention are of the type which are known to promote ice nucleation and a use of such microorganisms makes it possible to make snow at much higher temperatures than are ordinarily possible. Further, there is also disclosed a method for the recovery, in a dry form, of microorganisms that have ice nucleating activity from a medium containing the microorganisms that are grown in a conventional manner.

In U.S. Pat. No. 4,706,463, there is disclosed a method for recovering microorganisms that have ice nucleating activities. In this method, the temperature of the fermentation medium which contains *Pseudomonas syringae* is brought to a temperature of about 15° C. or less, a concentrate of said microorganism is formed and the concentrate is cooled to form frozen pellets, which is then frozen dried at a temperature below 25° C.

In U.S. Pat. No. 4,796,805, there is disclosed a method for making ice using ice nucleating microorganisms. The method comprises the steps of forming an aqueous suspension of ice nucleating microorganism, introducing the suspension into a water source to form an ice nucleated water source at a temperature below about 13° C. and distributing and freezing the ice nucleated water source. However, it was found that if the said suspension was allowed to stand at a temperature of 21° C. for about 24 hours, it completely lost the ice nucleating activity.

All of these prior arts are directed to prevent the employed ice nucleating microorganisms from losing their activities at room temperature.

Ice nucleating microorganisms that had been employed in these inventions mentioned above are for example Pseudomonads, particularly *P. syringae*. The preferred microorganism is *P. syringae* ATCC 53543 deposited on Sep. 23, 1986 with American Type Culture Collection. Another suitable examples of microorganisms that have ice nucleating activity are *P. syringae* KCTC 1832 deposited with Korean Collection for Type Cultures in Korea and *P. syringae* IFO 3310 deposited with Institute for Fermentation, Osaka in Japan.

Mr. L. R. Maki and his coworkers first discovered an ice nucleating microorganism in 1974(L. R. Maki et al., Applied Microbiology Vol. 28, p456, 1974), and thereafter many ice nucleating microorganisms have been extracted from leaves of various plants.

Examples of microorganisms having ice nucleating activity are *Pseudomonas syringae, Pseudomonas fluorcens, Pseudomonas pici, Pseudomonas coronafaciens, Pseudomonas viridiflava, Erwinia herbicola, Erwinia uredovara, Erwinia ananas* and *Xanthomonas campestris. Pseudomonas syringae*, among others, has higher ice nucleating activity and has been widely employed in the industry.

Unfortunately, however, these microorganisms are not stable and easily lose their ice nucleating activities at room temperature. As a result, in order to retain their ice nucleating activities, these microorganisms should be cultured, recovered and dried only at low temperature. Further, the suspension of these microorganisms also needs to be stored at low temperature.

Besides, in case that these ice nucleating microorganisms are employed for the ice production of an industrial scale, a large amount of microorganism cells are needed and these microorganisms should be maintained at low temperature during culture, recovery and drying process, transport and storage. These restrictions increase the cost and make the processes complex. Accordingly, there has been a need to provide a new strain which has ice nucleating activity at a higher temperature, for example at room temperature.

The present inventors had made researches to provide a new strain which has nucleating activity even at room temperature and as a result thereof could provide *Pseudomonas syringae* SO754 retaining ice nucleating activity stably at room temperature. *Pseudomonas syringae* SO754 of the invention retains high activity during the fermentation, recovery and drying steps and during transport and the storage.

SUMMARY OF THE INVENTION

Therefore, an object of the present invention is to provide a new strain which has ice nucleating activity at a temperature below about 25° C.

And an other object of the present invention is to provide an improved method for making ice at room temperature using said strain.

DETAILED DESCRIPTION OF THE INVENTION

Ice nucleating microorganisms may be extracted from the leaves of the frosted plant. These microorganisms are subjected to mutations to select a mutant still having ice nucleating activity at room temperature. The mutation and selection procedures are as follows.

Isolation of ice nucleating microorganisms

The leaves of the frosted plant were washed with a physiological solution and then the obtained solution was cultured in the nutrient agar medium which contains 0.3% of meat extract, 0.5% of peptone, 2.5% of glyceral and 1.5% agar at a temperature of about 30° C. for 2 days.

Thereafter, for the first isolation, the fermentor was moved to the freezer of −4° C. and maintained there for about 10 minutes. And strain colonies which showed ice nucleation were isolated.

Each of 75 isolated colonies was cultured at a temperature of 30° C. And then strains showing the highest ice nucleating activity were secondly isolated. The second isolation was carried out by comparing ice nucleating activities of all the colonies.

The ice nucleating activity was determined as follows: The isolated strains were cultured in a nutrient liquid medium which contains 0.3% of meat extract, 0.5% of pepton and 2.5% of glycerol at 30° C. for 24 hours. The cultured strains were recovered and then suspended in 50 mM phosphate buffer solution(pH 7). Under this condition, ice nucleating activity could be determined by measuring the temperature at which ice nucleation was observed.

Ice nucleating activity was determined with the Freezing nucleus spectrometer(Mitsuwa model K-1, Japan) by the method of Mr. Vali (Vali, G.: J. Atmos. Sci., 28, pp402–409, 1971).

From 75 colonies, one colony which had the highest ice nucleating activity was isolated, which was used as a parent strain to obtain an improved mutant strain.

The identification of parent strain

The identification of parent strain was carried out by following the method of Mr. Krieg(Krieg, N. R. : Bergey's manual of systematic bacteriology, Vol 1, 1984) and morphological, fermentative and physiological characteristics are shown in Tables 1 and 2.

From the results of Tables 1 and 2, the parent strain was identified as *Pseudomonas syringae*, and designated as *Pseudomonas syringae* SO7.

TABLE 1

The morphological and fermentative characteristics of the parent strain SO7

| Morphology | short rod |
|---|---|
| Size | 0.7~1.0 × 1.2~1.6 μm |
| Gram-stain | negative |
| Mobility | positive |
| Color of colony | light yellow-white |
| Oxygen requirement | aerobic |
| Optimum growth temperature | 28° C. |
| Fluorescent pigment | positive |
| Growth at 41° C. | negative |
| Levan production | positive |
| Arginine degradation | negative |
| Oxy-Meige reaction | negative |
| Denitrification | negative |
| Gelatin liquefaction | positive |
| Startch hydrolysis | negative |

TABLE 2

The physiological characteristics of the parent strain SO7

| Carbon source | Availability | Carbon source | Availability |
|---|---|---|---|
| Glucose | + | L-Alanine | + |
| D-Ribose | ± | D-Alanine | − |
| L-Arabinose | ± | L-Leucine | − |
| D-Mannose | ± | L-Histidine | − |
| D-Fructose | ± | L-Tyrosine | − |
| Raffinose | + | L-Tryptophan | − |
| Fumarate | + | Putrescine | + |
| Sucrose | ± | Sarcosine | + |
| Saccharate | −' | Linolenate | − |
| Valerate | + | Ascorbate | + |
| Pyruvate | + | Lecithin | − |
| Sorbitol | ± | Asparagine | − |

Preparation of mutant

The parent strain SO7 isolated as described above, had considerably high ice nucleation activity at 30° C. But unfortunately its activity was not stable against heat. Therefore, for the purpose of preparing new ice nucleating microorganism having the increased stability to heat, the parent strain SO7 was mutated and treated with heat. And then, mutant whose ice nucleating activity was very stable to heat was screened by measuring its ice nucleating activity.

Mutation was carried out by conventional technique using ultraviolet rays as a mutagen.

*Pseudomonas syringae* SO7 was cultured in a nutrient glycerol medium at 30° C. until an exponential growth phase. The recovered strains were suspended in a physiological solution, streaked onto a nutrient glycerol agar and then irradiated with a ultraviolet ray until extinction rate of germ became 95%. Immediately thereafter, the fermentor was moved to a dark room of 30° C., where culture was carried out for 24 hours.

Living strain colonies were replicated using a sterilized velvet and cultured at 30° C. for 24 hours. Replica was placed on the cooling bath of −4° C. Of them, a few colonies which showed ice nucleation earlier than the others were isolated.

The ice nucleating activity of the isolated colonies were measured by Freezing nucleus spectrometer. Among them, the strains whose ice nucleating activities were high and retained at room temperature were selected. These strains were cultured in a nutrient glycerol medium at 30° C. for 48 hours and centrifuged. The recovered strain pellets were washed with a physiological solution and freeze-dried. The freeze-dried strain pellets were suspended in 50 mM phosphate buffer solution(pH 7.0) and maintained in constant temperature bathes each of which temperature was 40° C., 35° C., 30° C., 25° C., 20° C., 10° C. and 4° C. respectively. After 24 hours, their activities were measured using Freezing nucleus spectrometer.

In these manner, a mutant whose activity was the highest and stable at room temperature was identified and designated as *Pseudomonas syringae* SO754. *Pseudomonas syringae* SO754 was deposited on July 19, 1993 in accordance with the Budapest Treaty with Korean Culture Culture Center of Microorganisms (KCCM), Department of Food Engineering, College of Engineering Yonsei University, Sodaemun-gu, Seoul 120-749, Korea and given an accession number KCCM-10039.

The mutant according to the present invention shows the same microbiological characteristics as those of the parent strain SO7 except the former strain retain its high ice nucleating activity at high temperature, and can be cultured in a fermentation medium which is commonly employed for the culture of *Pseudomonas syringae* and contains a suitable nitrogen and carbon source and inorganic salts under the controlled pH. These compositions of fermentation medium and culture conditions can be optimized without difficulty by any one skilled in the art.

Although the largest amount of solid ice nucleating microorganisms which had been used in the prior art can be collected at 28°~30° C., these microorganisms lose their activities at this range of temperature. Therefore they should be cultured at a low temperature below about 21° C.

However, the mutant according to the present invention shows good ice nucleating activity at a temperature below 60° C., particularly at a temperature below 40° C.

PREFERRED EMBODIMENTS OF THE INVENTION

The present invention shall be illustrated in more detail by way of the following examples. The following examples are merely illustrative and it should be understood that the present invention is not limited to these Examples.

EXAMPLE 1.

Five samples(A, B, C, D and E) of *Pseudomonas syringae* SO754 (KCCM-10039) were cultured for 24 hours in a 3 liter fermentor containing nutrient glycerol medium [0.3% of meat extract, 0.5% of peptone and 0.5% of glycerol] at the aeration of 1.0 VVM and pH of about 6.0. The culture temperatures were 15° C. (sample A), 21° C. (sample B), 25° C. (sample C), 28° C. (sample D) and 30° C. (sample E), respectively.

After culture was completed, broths were centrifuged and pellets were collected. The collected pellets were suspended in 50 mM phosphate buffer solution(pH 7.0) and their ice nucleating activities were determined by Mr. Vail's technique(Vail, G. J. : Atomos. Sci., 28, pp402–409, 1971). Ice nucleating activity is determined by measuring the temperature(T50%) at which 50% of total amount of sample was frozen.

The activity of sample A(T50%) was −2.6° C.; sample B, −2.5° C.; sample C, −2.8° C.; sample D, −2.8° C.; and sample E, −3.0° C.

COMPARATIVE EXAMPLE 1.

In this Example, the procedure of Example 1 was repeated except that Pseudomonas syringae ATCC 53,543 was used.

The activity of sample A(T50%) was −2.7° C.; sample B, −2.8° C.; sample C, −3.5° C.; sample D, −4.2° C.; and sample E, −4.9° C.

The results in Example 1 and comparative Example 1 are shown in the following Table 3.

TABLE 3

| Sample | Culture Temperature | Ice nucleating activity(T50%) Example 1 | C. Example 1 |
|---|---|---|---|
| A | 15° C. | −2.6° C. | −2.7° C. |
| B | 21° C. | −2.5° C. | −2.8° C. |
| C | 25° C. | −2.8° C. | −3.5° C. |
| D | 28° C. | −2.8° C. | −4.2° C. |
| E | 30° C. | −3.0° C. | −4.9° C. |

EXAMPLE 2.

Four samples(F, G, H and I) of *Pseudomonas syringae* SO754(KCCM-10039) cultured at 28° C. by the procedure of Example 1, were dried with a spraying dryer until the final temperatures of the dried sample were 60° C.(sample F), 50° C.(sample G), 40° C.(sample H) and 30° C.(sample I), respectively.

The activity of dried sample F(T50%) was −5.2° C.; sample G, −4.1° C.; sample H, −3.6° C.; and sample I, −3.1° C.

COMPARATIVE EXAMPLE 2.

In this Example, the procedure of Example 2 was repeated except that *Pseudomonas syringae* ATCC 53,543 was used.

The activity of dried sample F(T50%) was −8.3° C.; sample G, −6.7° C.; sample H, −5.7° C.; and sample I, −3.8° C.

The results in Example 2 and comparative Example 2 are shown in the following Table 4.

TABLE 4

| Sample | Final temperature of dried sample | Ice nucleating activity(T50%) Example 2 | C. Example 2 |
|---|---|---|---|
| F | 60° C. | −5.2° C. | −8.3° C. |
| G | 50° C. | −4.1° C. | −6.7° C. |
| H | 40° C. | −3.6° C. | −5.7° C. |
| I | 30° C. | −3.1° C. | −3.8° C. |

EXAMPLE 3.

The dried strain of sample H(final temperature: 40° C.) obtained in Example 2 was suspended into the distilled water to form a suspension. Several samples(Sample Nos. were a, b, c, d, e, f and g) of this suspension were placed for 12 hours in a constant temperature bath whose temperature was 4° C., 10° C., 20° C., 25° C., 30° C., 35° C. and 40° C., respectively.

Ice nucleating activity of the samples are expressed as a percentage of remaining activity to that of Example 2 and the results are shown in the following Table 5.

COMPARATIVE EXAMPLE 3.

In this Example; the procedure of Example 3 was repeated except that the dried strain of sample H(final temperature: 40° C.) obtained in Comparative Example 2 was used.

Ice nucleating activities of the samples are expressed as a percentage of remaining activity to that of C. Example 2 and the results are shown in the following Table 5.

TABLE 5

| Sample | Temperature of sample | Total Ice nucleating activity of remaining sample(%) Example 3 | C. Example 3 |
|---|---|---|---|
| a | 4° C. | 99.8% ± 5.4 | 92.3% ± 2.5 |
| b | 10° C. | 91.2% ± 3.1 | 89.6% ± 3.1 |
| c | 20° C. | 97.6% ± 2.3 | 81.5% ± 3.4 |
| d | 25° C. | 95.4% ± 2.9 | 75.3% ± 5.2 |
| e | 30° C. | 89.7% ± 3.4 | 54.3% ± 6.7 |
| f | 35° C. | 82.3% ± 3.3 | 25.9% ± 7.3 |
| g | 40° C. | 75.1% ± 5.1 | 11.1% ± 6.4 |

As shown in Table 3~5, the novel mutant SO754(KCCM-10039) of the present invention has higher activity than ATCC 53,543 over the wide range of temperature and more particularly it shows much higher ice nucleating activity at a temperature range of 25°~40° C.

The invention has been described in detail with particular reference to preferred embodiments thereof, but it will be understood that variations and modifications can be effected within the spirit and scope of the invention.

What is claimed is:

1. A biologically pure culture of a microorganism *Pseudomonas syringae* which has all the identifying characteristics of strain KCCM-10039 having ice nucleating activity at room temperature.

2. A biologically pure culture of the microorganism *Pseudomonas syringae* KCCM-10039, wherein said culture retains ice nucleating activity when cultured or stored in solution at room temperature.

3. The culture of claim 2, wherein said microorganism retains ice nucleating activity when cultured or stored in solution at a temperature up to about 30° C.

4. The culture of claim 2, wherein said microorganism retains ice nucleating activity when cultured or stored in solution at a temperature up to about 25° C.

5. The culture of claim 2, wherein said microorganism retains ice nucleating activity when cultured or stored in solution at a temperature up to about 21° C.

6. The culture of claim 2, wherein said microorganism retains ice nucleating activity when dried to a temperature of up to about 60° C.

7. The culture of claim 2, wherein said microorganism retains ice nucleating activity when dried to a temperature of up to about 50° C.

8. The culture of claim 2, wherein said microorganism retains ice nucleating activity when dried to a temperature of up to about 40° C.

9. The culture of claim 2, wherein said microorganism retains ice nucleating activity when dried to a temperature of up to about 30° C.

10. A method for forming ice particles using an ice nucleating microorganism, which comprises the steps of:
    (a) forming an aqueous suspension of an effective amount of a biologically pure culture of an ice nucleating microorganism *Pseudomonas syringae* KCCM-10039;
    (b) introducing said aqueous suspension into a water source whose temperature is maintained below about 25° C. to form a mixture;
    (c) cooling said mixture until ice is formed; and
    (d) distributing and freezing said mixture.

11. The method of claim 10, wherein said aqueous suspension is maintained or stored in solution at a temperature up to about 20° C.

12. The method of claim 10, wherein said aqueous suspension is maintained or stored in solution at a temperature up to about 25° C.

13. The method of claim 10, wherein said aqueous suspension is maintained or stored in solution at a temperature up to about 35° C.

14. The method of claim 10, wherein said aqueous suspension is maintained or stored in solution at a temperature up to about 35° C.

\* \* \* \* \*